United States Patent [19]

Weiss

[11] Patent Number: 4,549,134
[45] Date of Patent: Oct. 22, 1985

[54] MOISTURE PROBE AND TECHNIQUE

[75] Inventor: Thomas M. Weiss, Midland, Mich.

[73] Assignee: The Dow Chemical Company, Midland, Mich.

[21] Appl. No.: 648,902

[22] Filed: Sep. 7, 1984

Related U.S. Application Data

[63] Continuation of Ser. No. 475,998, Mar. 17, 1983, abandoned, which is a continuation of Ser. No. 886,853, Mar. 15, 1978, abandoned.

[51] Int. Cl.$^4$ ............................................. G01R 27/26
[52] U.S. Cl. .............................. 324/61 R; 324/65 R; 324/71.1; 338/34; 338/35
[58] Field of Search ................. 338/34, 35; 324/61 R, 324/61 P, 65 R, 65 P, 71.1, 439; 204/430, 409

[56] References Cited

U.S. PATENT DOCUMENTS

| | | | |
|---|---|---|---|
| 1,383,233 | 6/1921 | Parsons et al. | 324/71.1 |
| 2,830,945 | 4/1958 | Keidel | 204/195 |
| 3,001,918 | 9/1961 | Czuha, Jr. | 204/430 |
| 3,105,214 | 9/1963 | Blythe et al. | 338/35 |
| 3,291,705 | 12/1966 | Hersch | 204/409 |
| 3,432,403 | 3/1969 | Glass et al. | 204/260 |
| 3,671,912 | 6/1972 | La Sota | 338/34 |
| 3,710,244 | 1/1973 | Rauchwerger | 324/61 R |
| 3,810,389 | 5/1974 | Jason | 338/35 |
| 4,083,765 | 4/1978 | Lawson | 204/430 |

Primary Examiner—Ernest F. Karlsen
Assistant Examiner—Kevin D. O'Shea

[57] ABSTRACT

A superior moisture probe and technique for assaying liquid and gas streams for moisture concentration in the parts per million (ppm) range, comprises an emf source connected across a pair of adjacent conductive probes separated by a sulfonated aliphatic fluorocarbon membrane, the combination being immersed in the fluid of interest, or in a sealed headspace associated therewith, the former being the preferred mode. With a D.C. emf, the resistance change of the probe, or a value proportional therewith is monitored, and from that value $H_2O$ concentration is deduced. With an A.C. emf, capacitance, A.C. resistance, and/or impedance of the described probe structure varies proportionately with the concentration of $H_2O$ in the membrane, and is monitored directly or indirectly to deduce $H_2O$ concentration. In the latter form of the invention, the conductive components of the probe are desirably clad by a corrosion resistant, impermeable polymeric coating, and in such form, the use of expensive noble metal components for the probe is less critical, and substitution with less expensive conductive materials is thus practical for certain applications.

29 Claims, 5 Drawing Figures

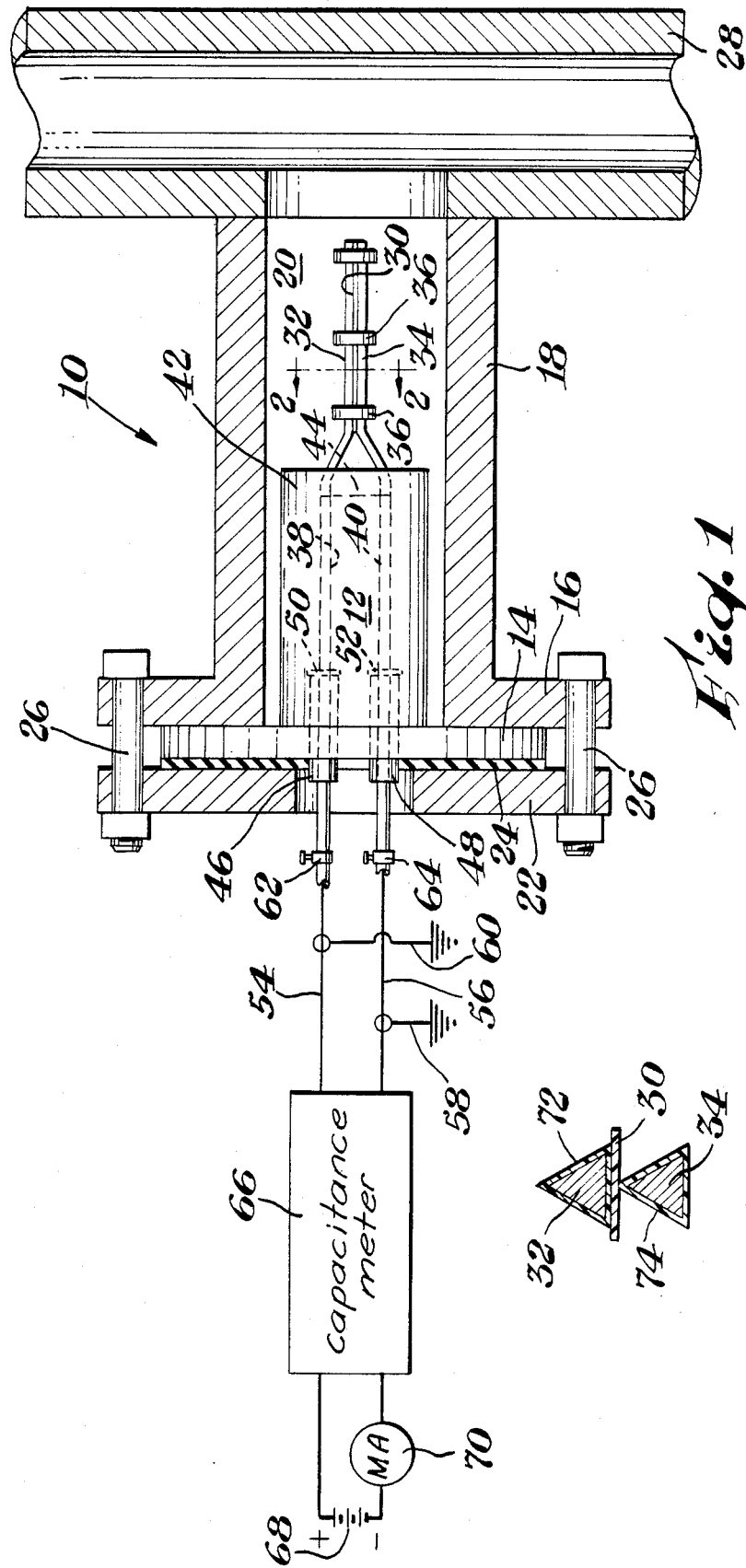

MOISTURE PROBE AND TECHNIQUE

CROSS-REFERENCE TO RELATED APPLICATION

This is a continuation of abandoned application Ser. No. 475,998, filed Mar. 17, 1983, which is a continuation of abandoned application Ser. No. 886,853, filed Mar. 15, 1978.

FIELD OF THE INVENTION

The invention relates to instrumentation and techniques for assaying the moisture content of various electrolytic and non-electrolytic fluids. More particularly, the invention relates to a direct water concentration analysis technique and instrument, that is extremely simple and durable, and yet highly sensitive, and which is used in a direct measuring system without requiring any sample handling whatsoever.

BACKGROUND OF THE INVENTION

The classic technique for determining moisture content in fluids requires sample handling in the mode described in U.S. Pat. No. 2,830,945, to Keidel, which is considered exemplary of the technique. Here the sample is taken and passed through a flow meter to determine volume. Essentially all water is then extracted from the sample onto an absorbent film. Substantially complete hydrolysis is practiced to reduce the extracted water to its components $O_2$ and $H_2$, and the expended current is related to the sample volume to quantitate the $H_2O$ concentration.

Obvious disadvantages of the technique include fouling problems, since total electrolysis is practiced. While sample filtering is useful to reduce the scope of the problem, and is in fact, required for most applications, the step itself introduces even further complexity into the technique, and is usually not entirely successful. More objectionable is the slow response required since the technique is based on sampling rather than a direct analysis. What the art refers to as "combination effects" or non-selective reactions are also produced in the hygrometer cell, thus producing a response interference that lessens precision. Also, the technique is limited further in application by the percentage of $H_2O$ concentration. Hence, for an analysis above 10,000 ppm, the technique is oftentimes not suitable.

The only known prior direct measurement technique, thus avoiding some of the problems with the earlier Keidel mode, is based on a novel probe construction using an aluminum base, a porous aluminum oxide layer thereon, and a thin gold coating deposited on the oxide layer. The device is available from Panametrics, a subsidiary of Esterline Corporation. The principle relies on the selective transportation of water molcules through the thin gold plating and into the porous aluminum oxide coating. Impedance changes in the probe thus produce a value from which $H_2O$ concentration can be deduced. The device, however, is not useful for a diverse number of industrial chemical and other process stream analysis simply because it is not chemically durable. Also, while the principle might be possibly expanded to use other membrane constructions, such as the aliphatic fluorocarbon membranes mentioned in the abstract (which have been suggested for the Keidel electrolysis technique), actual experiments (not considered prior art) have failed to establish suitability of purpose because of material expansion problems.

The Invention

The invention utilizes a membrane material, sulfonated aliphatic fluorocarbon polymers, as a selective water absorber and desorber, i.e., water concentrator, but in a manner departing from the principles of the Keidel technique, and the transport technique through a gold or noble metal plating as described, supra. The new combination and technique more specifically advance the state of the art, while avoiding the serious limitations which beset the two prior described modes. The invention is particularly distinguished by an extremely fast response time, analysis simplicity, and fouling and corrosion resistant qualities, that make it highly suitable for chemical, on-line process stream monitoring, for which satisfactory $H_2O$ sensors have not been available in the past.

Basically the invention comprises a selected membrane, most optimally a Nafion ® polymer, immersed and exposed directly in the gas or liquid stream to be monitored. Where requirements might dictate otherwise, the membrane may be placed rather in a sealed headspace. The former positioning, however, is preferred for fastest response time. A pair of capacitor plate means (for the A.C. mode) or terminals for the D.C. mode) are in pressed contact on each side of the membrane. Depending on the amount of water that is concentrated in the membrane, a distinguishing change in the resistance across the membrane is observed, for analysis by the D.C. mode. A similar distinguishing change in the capacitance, A.C. resistance, and/or impedance of the probe is produced using an A.C. emf. These values have been found highly discriminating of the actual concentration of $H_2O$ in the monitored stream with quantitation in the ppm range thus frequently possible. The instrument is simply calibrated, such that the monitored and changing electrical properties of the probe, or properties determinable therefrom, as for example, power factor, can be read and compared against a calibration curve to rapidly deduce the actual $H_2O$ content in the monitored fluid.

As can be readily appreciated, since the instrument's calibration is predominantly dependent on mostly a single major influencing factor (pressure for gases, temperature for liquids), the system does not require a great deal of expertise to operate. Thus, it is ideally suited to in plant process monitoring. Moreover, since it does not utilize the electrolysis mode of Keidel, filtering is rarely, if ever, required, or even to be recommended. Also, since in the preferred mode (A.C.) all components which are exposed and immersed in the process stream are polymeric or polymeric clad, far less limitations with respect to corrosion influencing errors and drift are experienced. Since voltages can be quite low (below about 1.23 V for the D.C. mode) to avoid electrolysis, it is also readily apparent that typical combination reactions, induced under electrolysis conditions, are substantially if not altogether avoided by the instrumentation and technique of this invention.

Yet further advantageous and the cognate benefits of the invention are evident and made manifest by reference to the description of the preferred embodiment below, taken in conjunction with the accompanying drawing wherein:

FIG. 1 shows a moisture probe constructed in accordance with the teachings hereof, and represents a preferred form of the invention;

FIG. 2 is a cross-sectional view taken along reference line 2—2 of FIG. 1; and

Figure 3:
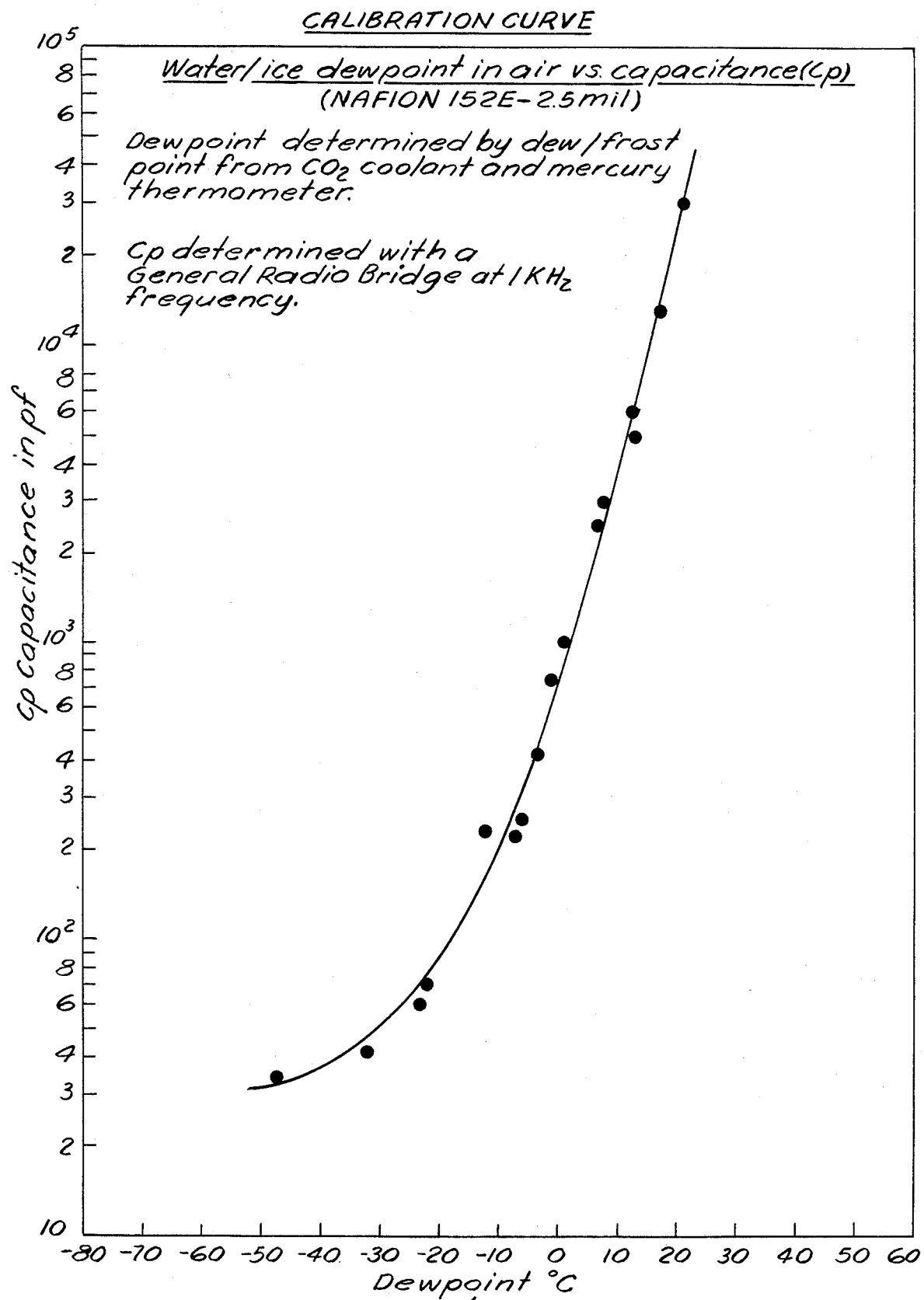
Figure 4:
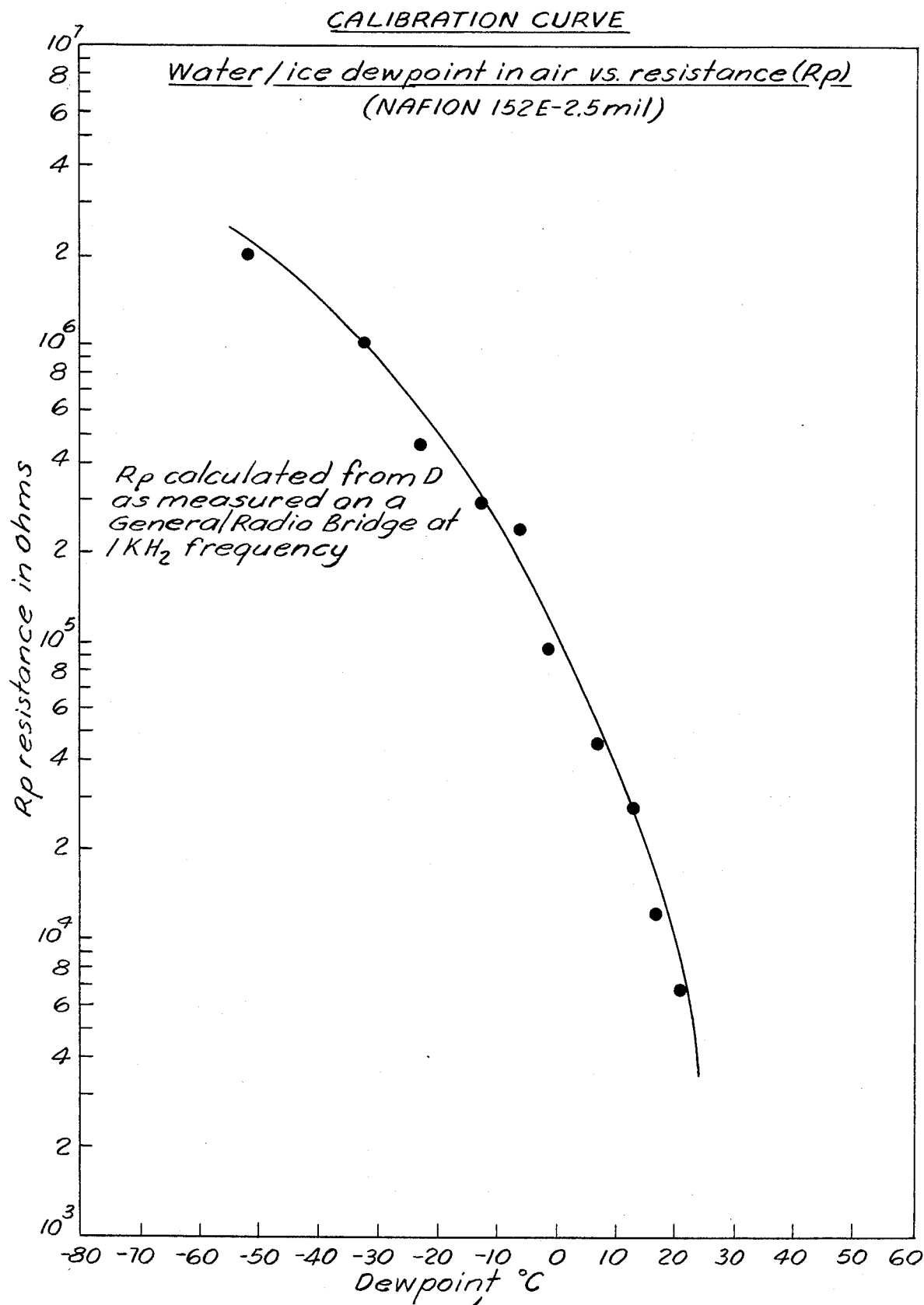
Figure 5:
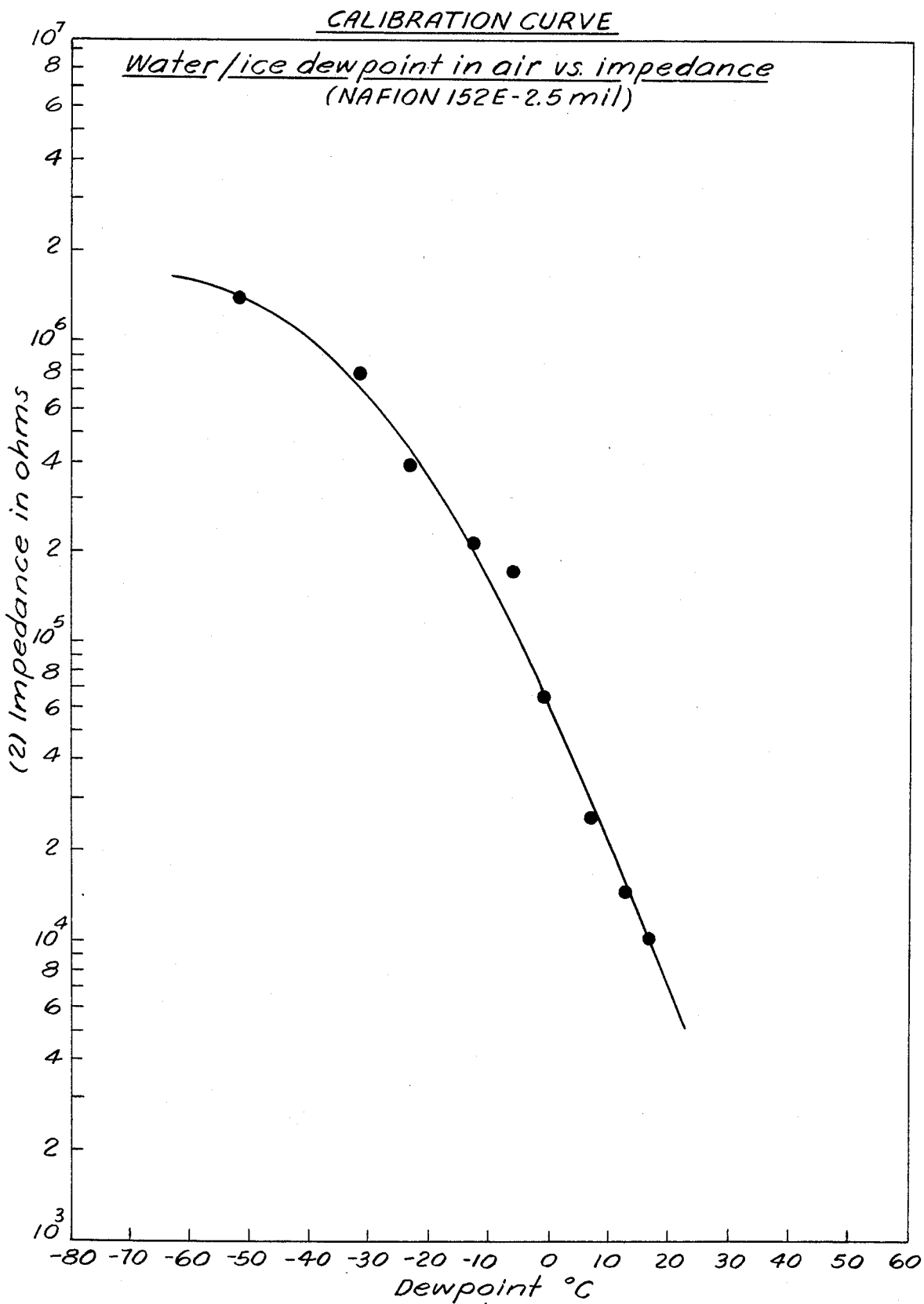

FIGS 3-5 reproduce certain calibration curves used to deduce actual moisture content from the monitored values reported by a modified and hereinafter described electronic circuit associated with the FIG. 1 form of the invention.

DETAILED DESCRIPTION OF THE INVENTION

A preferred moisture probe or water vapor pressure sensor, constructed in accordance with the inventive principles is shown in FIG. 1, as generally designated by Reference Numeral 10. The moisture sensor embodies a plug or probe body 12 comprising an electrical insulator, and also selected for optimum corrosion resistance. A preferred material is glass filled Teflon ® polymeric material. The plug is constructed with a flange 14 that is seated with the flanged end 16 of a T-fitting 18 to form a hermetically sealed cavity 20 in which the sensor 10 operates. The plug is fastened to the T-fitting by a compression plate 22, gasket 24, preferably of silicone rubber, and bolt fasteners 26. The T-fitting at its forward end opposite flanged end 16, is welded or otherwise hermetically joined to the side of a process stream pipe 28. The liquid or gas process stream thus enters the sealed cavity 20 immersing the sensor therein.

The operating components of the sensor include a polymeric membrane 30. The electrical properties vary dramatically in proportion to the amount of moisture absorbed and concentrated in the membrane. A pair of elongated, electrically conductive members or elements or probes 32 and 34 are in pressed contact on each side of the membrane. For the A.C. mode, the members 32, 34 are aptly described as capacitance plate means, and for the D.C. mode of operation, terminals. Maximum response time is obtained by using an ultra-thin membrane, preferably of low molecular weight. Preferred membrane thickness is under 10 mils, and most preferred under 5 mils. Membranes of between about ½ mil to about 2.5 mils are considered especially satisfactory for the purpose of the invention.

Maximum response time is also significantly facilitated by obtaining good surface exposure of the membrane to the fluid in which it is immersed. To this end, a preferred probe geometry is shown in FIG. 2. In the geometry illustrated probes 32, 34 are given a triangular configuration, with the flat side of one (probe 32) pressed against the membrane for good mechanical stability, and the edge of the opposite probe 34 engaging the opposite side of the membrane to achieve maximum surface exposure. The membrane may be held simply by mechanical fasteners such as several O-rings 36 that are slipped over the probes 32, 34, thus mechanically compressing the membrane between the probes.

The probes 32, 34 are returned to the space exterior of the sealed cavity 20 through axially aligned and laterally spaced apart openings 38, 40 in plug 12, the openings being spaced to minimize capacitance effects. The probes are parted by bending just before the forward internal end 42 of the plug, thus diverging apart and entering first a plug recess 44 and then proceeding straight through the openings to the space external of the plug. Hollow packing nuts 46, 48 are threaded into the opposite end of plug 12, each about a respective probe 32, 34 and engage packing glands, preferably in the form of O-rings 50, 52, respectively. The compressed O-rings thus seal the space between the plug openings and probes 32, 34, respectively.

Shielded wires 54, 56 (to avoid capacitance effects), are each grounded at 58, 60, and are brought into electrical contact with the exposed ends of the probes and secured by fastener means 62, 64, respectively. The shielded wires connect in the most preferred mode to a capacitance meter 66, adapted to apply an A.C. emf across the probes 32, 34, and to monitor the changing electrical properties of the immersed membrane. A Robertshaw Model 160-BX capacitance meter is suitable for the intended purpose. The Robertshaw capacitance meter is powered by a D.C. input source 68, and preferably operated at about 26 volts D.C., although not critical. The capacitance meter converts the changing capacitance properties of the membrane to an output D.C. current that is read on an ammeter 70.

Polymeric membrane materials suitable for use in the invention evidence dramatic changes in electrical properties, based on relatively small changes in the moisture concentrated in the membrane, as illustrated most effectively in the calibration curves of FIGS. 3-5. These curves were generated using a General Radio Bridge at 1KH$_z$ frequency, substituted for the capacitance meter described, supra, and capable of performing, in addition to the monitoring of capacity property changes, also A.C. and D.C. resistance, and variable impedance response.

Describing first the generation of the capacitance calibration curve, FIG. 3, using the A.C. mode, gas containing variable amounts of moisture, as determined by dew point, is passed by the probe, and the capacitance response vis a vis the dew point is recorded. Sufficient points are thus recorded to produce the curve shown. Impedance, A.C. resistance, and D.C. resistance, are similarly determined. From these curves, practically any property such as the named capacitance, A.C., D.C. resistance, and impedance, together with electrical properties determinable therefrom such as power factor, etc. may hence be monitored to deduce the water vapor pressure. More particularly the range of water vapor pressure for a volume at 1 atmosphere pressure can be expressed in parts per million (ppm) using a standard conversion table, such as the General Eastern Water Vapor Conversion Table, by General Eastern Corporation of 36 Maple Street, Watertown, Massachusetts, 02172. As such, the moisture probe, used to generate the data of FIG. 3 can defect from 44—24,000 ppm; the moisture probe used to generate the data of FIG. 4, can detect from 14—25,000 ppm; and the moisture probe used to generate the data of FIG. 5 can defect from 15—23,000 ppm.

Membrane materials which admirably satisfy the requirements of the water vapor pressure sensor of the invention are selected from the class of sulfonated aliphatic fluorocarbon polymers which exhibit the response properties as described previously, or properties closely similar thereto. The most preferred materials are available under the trademark Nafion, and these polymers are described in some detail in the publication *DuPont Innovation*, Vol. 4, No. 3, Spring 1973, which is hereby incorporated by reference.

An especially significant property of the preferred Nafion ® materials, a perfluorosulfonic acid substituted polytetrafluoroethylene, is selective absorbtion of water molcules, to the exclusion of common chemical products and solvents. A listing of the selectivity of the preferred membrane material, with respect to many such products and solvents, is found in the *American Industrial Hygiene Association Journal,* November, 1974, page 735 et seq., also hereby incorporated by reference. It should be observed that certain alcohols, water-soluble ethers, amines and ketones, are at least partially absorbed by the membrane. Here unsuitability of the water vapor sensor hereof should not be judged, since the effect can be diminished by accepted and properly observed calibration techniques.

In respect to other facets of the invention, it should also be observed that with the A.C. mode, it is highly beneficial to clad the probes, most desirably of a noble metal, preferably platinum, with an impervious polymeric coating, as shown and indicated in FIG. 2 in the form of polymeric coatings 72, 74. Preferred coatings may be made by spray painting or dipping the electrodes in a suitable Teflon ® paint or hardenable dipping solution. The use of the coatings 72, 74 thus advantageously permits, in some applications of lesser corrosion difficulties, the use of probes constructed of inexpensive conductive materials such as copper, brass, aluminum, graphite, etc. In addition, expanded utility to the analysis of electrolytes is achieved by insulating the probes through applying polymeric coatings thereto. For the D.C. mode, such coatings may be beneficially employed where polymeric conductive coatings are applied. Thus polymeric clad electrodes of suitable ionomer polymers, or polymers filled with conductive powders may be utilized to achieve a suitable clad probe construction adapted to the D.C. mode of analysis.

The shape of the probes and membrane is not critical, provided the membrane is exposed for fast response. Alternate probe geometry considered highly adaptable to the invention would be a screen/plate combination or a screen/screen thus achieving maximum exposure of the membrane for fast response time.

WHAT IS CLAIMED IS:

1. Apparatus for sensitivity detecting, quantitatively, a range of concentrations, particularly trace concentrations of water in diverse fluids of interest, with utility for quantitating in the low ppm range, comprising in combination:

a capacitance element comprising a pair of capacitor plates between which there is disposed a membrane;

said membrane comprising a sulfonated aliphatic fluorocarbon polymer, the capacitance element having the property to produce detectable capacitance change with changes in water concentration in air at least over the range of about 24,000 ppm to about 44 ppm;

means for impressing a voltage below the voltage level required for electrolysis from the first capacitor plate through the membrane to the second capacitor plate and thereby causing a change in the capacitance of the membrane dependant upon the water concentration in the fluid of interest; and means for detecting capacitance change of the capacitance element for purposes of determining the concentration of water in the fluid of interest.

2. Apparatus for sensitively detecting, quantitatively, a range of concentrations, particularly trace concentrations of water in diverse fluids of interest, with utility for quantitating in the low ppm range, comprising in combination:

a resistance element comprising a pair of terminals between which there is disposed a membrane;

said membrane comprising a sulfonated aliphatic fluorocarbon polymer, the resistance element having the property to produce detectable resistance change with changes in water concentration in air at least over the range of about 25,000 ppm to about 14 ppm;

means for impressing a voltage below the voltage level required for electrolysis from the first terminal through the membrane to the second terminal and thereby causing a change in the resistance of the membrane dependant upon the water concentration in the fluid of interest; and means for detecting resistance change of the resistance element for purposes of determining the concentration of water in the fluid of interest.

3. The apparatus of claim 2, wherein the voltage is a D.C. voltage.

4. Apparatus for sensitively detecting, quantitatively, a range of concentrations, particularly trace concentrations of water in diverse fluids of interest, with utility for quantitating in the low ppm range, comprising in combination:

an impedance element comprising a pair of terminals between which there is disposed a membrane;

said membrane comprising a sulfonated aliphatic fluorocarbon polymer, the impedance element having the property to produce detectable impedance change with changes in water concentration in air at least over the range of about 23,000 ppm to about 15 ppm;

means for impressing a voltage below the voltage level required for electrolysis from the first terminal through the membrane to the second terminal and thereby causing a change in the impedance of the membrane dependant upon the water concentration in the fluid of interest; and means for detecting impedance change of the impedance element for purposes of determining the concentration of water in the fluid of interest.

5. The apparatus of claim 1, whereby the plates have non-metallic, corrosion resistant cladding.

6. The apparatus of claim 2, whereby the terminals have non-metallic, corrosion resistance cladding.

7. The apparatus of claim 4, whereby the terminals have non-metallic, corrosion resistant cladding.

8. The apparatus of claim 1, whereby the membrane has a thickness within the range of about 0.5–10 mils.

9. The apparatus of claim 2, whereby the membrane has a thickness within the range of about 0.5–10 mils.

10. The apparatus of claim 4, whereby the membrane has a thickness within the range of about 0.5–10 mils.

11. The apparatus of claim 1, whereby the membrane comprises a perfluorosulfonic acid substituted polytetrafluoroethylene material.

12. The apparatus of claim 2, whereby the membrane comprises a perfluorosulfonic acid substituted polytetrafluoroethylene material.

13. The apparatus of claim 4, whereby the membrane comprises a perfluorosulfonic acid substituted polytetrafluoroethylene material.

14. A method for sensitively detecting, quantitatively, a range of concentrations, particularly trace concentrations of water in diverse fluids of interest, with utility for quantitating in the low ppm range, comprising the steps of:

disposing a capacitance element comprising a pair of capacitor plates between which there is disposed a membrane in a fluid of interest, said membrane comprising a sulfonated aliphatic fluorocarbon polymer, the capacitance element having the property to produce detectable capacitance change with respect to water concentration in air at least over the range of about 24,000 ppm to about 44 ppm;

impressing a voltage below the voltage level required for electrolysis from the first capacitor plate to the second capacitor plate and thereby causing a change in the capacitance of the membrane dependent on the water concentration in the fluid of interest; and detecting capacitance change of the capacitance element for purposes of determining the concentration of water in the fluid of interest.

15. A method for sensitively detecting, quantitatively, a range of concentrations, particularly trace concentrations of water in diverse fluids of interest, with utility for quantitating in the low ppm range, comprising the steps of:

disposing a resistance element comprising a pair of terminals between which there is disposed a membrane in a fluid of interest, said membrane comprising a sulfonated aliphatic fluorocarbon polymer, the resistance element having the property to produce detectable resistance change with respect to water concentration in air in the fluid of interest at least over the range of about 25,000 ppm to about 14 ppm;

impressing a voltage below the level required for electrolysis from the first terminal to the second terminal and thereby causing a change in the resistance of the membrane dependent on the water concentration in the fluid of interest; and detecting resistance change of the resistance element for purposes of determining the concentration of water in the fluid of interest.

16. A method for sensitively detecting, quantitatively, a range of concentrations, particularly trace concentrations of water in diverse fluids of interest, with utility for quantitating in the low ppm range, comprising the steps of:

disposing an impedance element comprising a pair of terminals between which there is disposed a membrane in a fluid of interest, said membrane comprising a sulfonated aliphatic fluorocarbon polymer, the impedance element having the property to produce detectable impedance change with respect to water concentration in air at least over the range of about 23,000 ppm to about 15 ppm;

impressing a voltage below the level required for electrolysis from the first terminal to the second terminal and thereby causing a change in the impedance of the membrane dependent on the water concentration in the fluid of interest; and detecting impedance change in the impedance element for purposes of determining the concentration of water in the fluid of interest.

17. The method of claim 16, wherein the voltage impressed on the membrane is a D.C. voltage.

18. The method of claim 14, further comprising the step of cladding the plates with a non-metallic, corrosion-resistant material.

19. The method of claim 15, further comprising the step of cladding the terminals with a non-metallic, corrosion-resistant material.

20. The method of claim 16, further comprising the step of cladding the terminals with a non-metallic, corrosion resistant material.

21. The method of claim 14, further comprising the step of using a membrane with a thickness in the range of about 0.5–10 mils.

22. The method of claim 15, further comprising the step of using a membrane with a thickness in the range of about 0.5–10 mils.

23. The method of claim 16, further comprising the step of using a membrane with a thickness in the range of about 0.5–10 mils.

24. The method of claim 14, further comprising the step of using a membrane comprising a perfluorosulfonic acid substituted polytetrafluoroethylene.

25. The method of claim 15, further comprising the step of using a membrane comprising a perfluorosulfonic acid substituted polytetrafluoroethylene.

26. The method of claim 16, further comprising the step of using a membrane comprising a perfluorosulfonic acid substituted polytetrafluoroethylene.

27. The method of claim 14, further comprising the step of disposing the membrane within a sealed headspace communicating with the fluid of interest.

28. The method of claim 15, further comprising the step of disposing the membrane within a sealed headspace communicating with the fluid of interest.

29. The method of claim 16, further comprising the step of disposing the membrane within a sealed headspace communicating with the fluid of interest.

* * * * *

UNITED STATES PATENT AND TRADEMARK OFFICE
CERTIFICATE OF CORRECTION

PATENT NO. : 4,549,134
DATED : October 22, 1985
INVENTOR(S) : Weiss

It is certified that error appears in the above—identified patent and that said Letters Patent is hereby corrected as shown below:

Column 1, line 57, delete "molcules" and insert --molecules--.
Column 2, line 12, insert --s-- to "vance".
line 28, insert --(-- after "terminals".
Column 3, line 45, insert --s-- to "purpose".
Column 4, line 68, delete "molcules" and insert --molecules--.
Column 5, line 41, delete "sensitivity" and insert --sensitively--.

Signed and Sealed this

Eighteenth Day of February 1986

[SEAL]

Attest:

DONALD J. QUIGG

Attesting Officer

Commissioner of Patents and Trademarks